United States Patent [19]

Klearman et al.

[11] Patent Number: 5,148,563
[45] Date of Patent: Sep. 22, 1992

[54] CUSTOM ORTHOTIC BRACING SYSTEM

[75] Inventors: Jeffrey D. Klearman, Chesterfield; Jeffrey J. Bierman, St. Louis; Lambert J. Pott; Glen E. Watson, Jr., both of Chesterfield, all of Mo.

[73] Assignee: Lake Medical Products, Inc., St. Louis, Mo. ; by said Jeff Bierman

[21] Appl. No.: 783,834

[22] Filed: Oct. 29, 1991

[51] Int. Cl.⁵ .............................................. A61F 5/37
[52] U.S. Cl. ........................................ 5/652; 5/653; 5/657; 5/633; 297/465; 297/485; 297/467; 128/874; 128/809
[58] Field of Search ............... 5/621, 633, 652, 653, 5/657; 297/464, 465, 467, 485, 458, 459; 128/845, 869, 870, 874; 602/19

[56] References Cited

U.S. PATENT DOCUMENTS

| | | | |
|---|---|---|---|
| 3,205,010 | 9/1965 | Schick | 297/458 X |
| 3,452,748 | 7/1969 | Caprio | 602/19 |
| 4,050,737 | 9/1977 | Jordan | 297/465 |
| 4,093,307 | 6/1978 | McLennan | 297/485 |
| 4,211,218 | 7/1980 | Kendrick | 128/870 X |
| 4,593,280 | 6/1986 | Miller | 128/869 X |
| 4,712,833 | 12/1987 | Swanson | 297/464 X |
| 4,898,185 | 2/1990 | Fuller | 297/485 X |
| 5,018,790 | 5/1991 | Jay | 297/959 X |
| 5,056,533 | 10/1991 | Solano | 128/845 |
| 5,076,264 | 12/1991 | Lonardo et al. | 128/874 X |

OTHER PUBLICATIONS

Two Pages of Color Photographs and Two Brochures on Blue Vinyl Colored Vest.
One Page of Color Photographs and One Brochure on Body Vest.

Primary Examiner—Michael F. Trettel
Attorney, Agent, or Firm—Rogers, Howell & Haferkamp

[57] ABSTRACT

A chair restraint for supporting a patient in a sitting position from a chair or the like includes an upper torso support member having an orthotic support panel readily removable therefrom. The orthotic support panel is made from a plastic which is readily deformable by a heat gun or the like such that it may be custom fit to surround the patient both from his back and sides to provide lateral support to the patient. The upper torso restraint member includes a pair of straps extending forwardly to wrap around the front of the patient to thereby secure the patient within the upper torso restraint member. A seat cushion member includes a flat panel stiffener to provide a firm base for the patient and an interior cushioning member which is inclined generally rearwardly to thereby cradle the patient within the restraint. A center divider member of cushioning material provides two separately defined areas for receiving the patient's legs. Straps are provided for securing the upper torso restraing member to the seat cushion member, and both of those members independently to the chair frame.

22 Claims, 3 Drawing Sheets

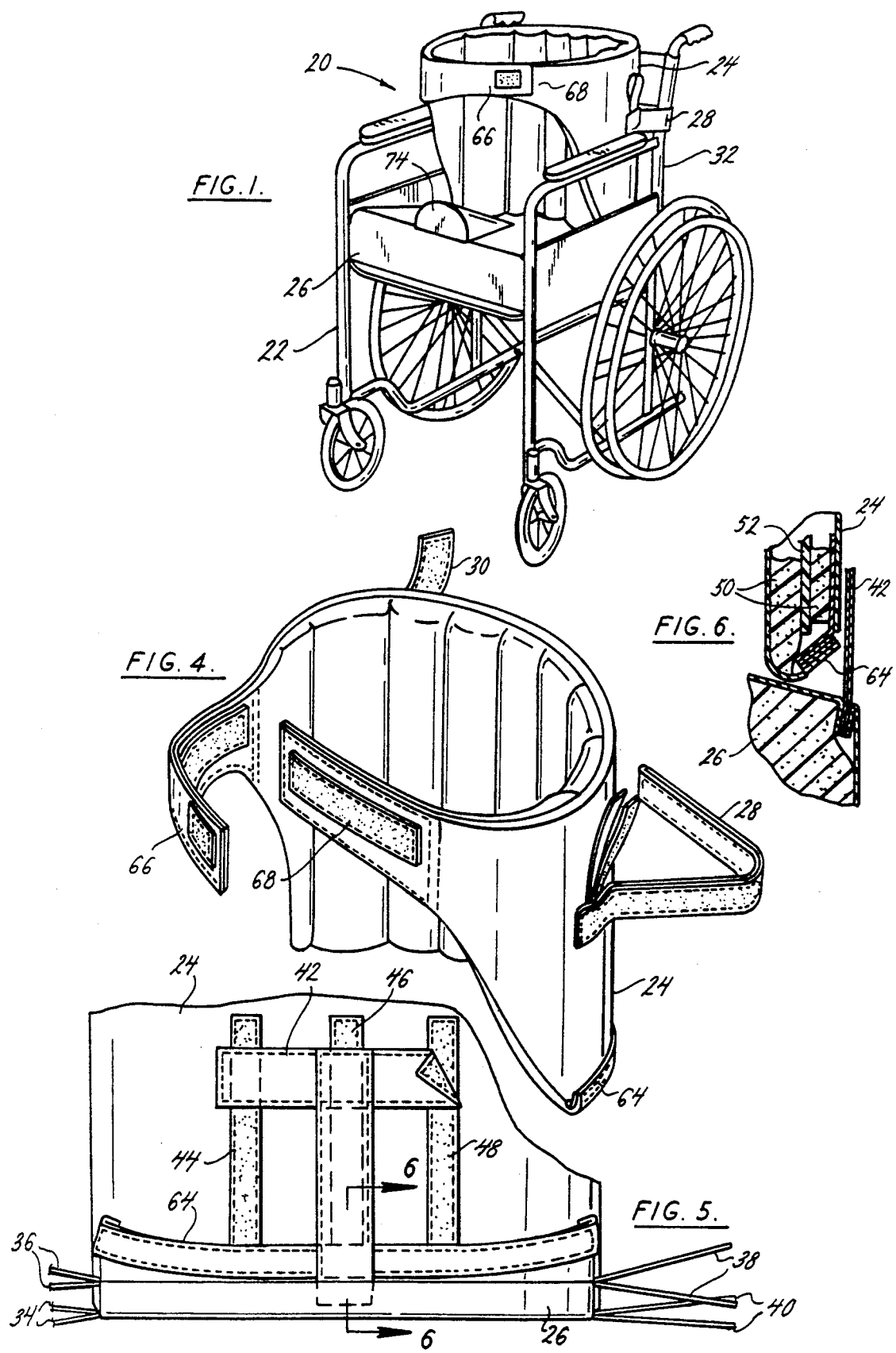

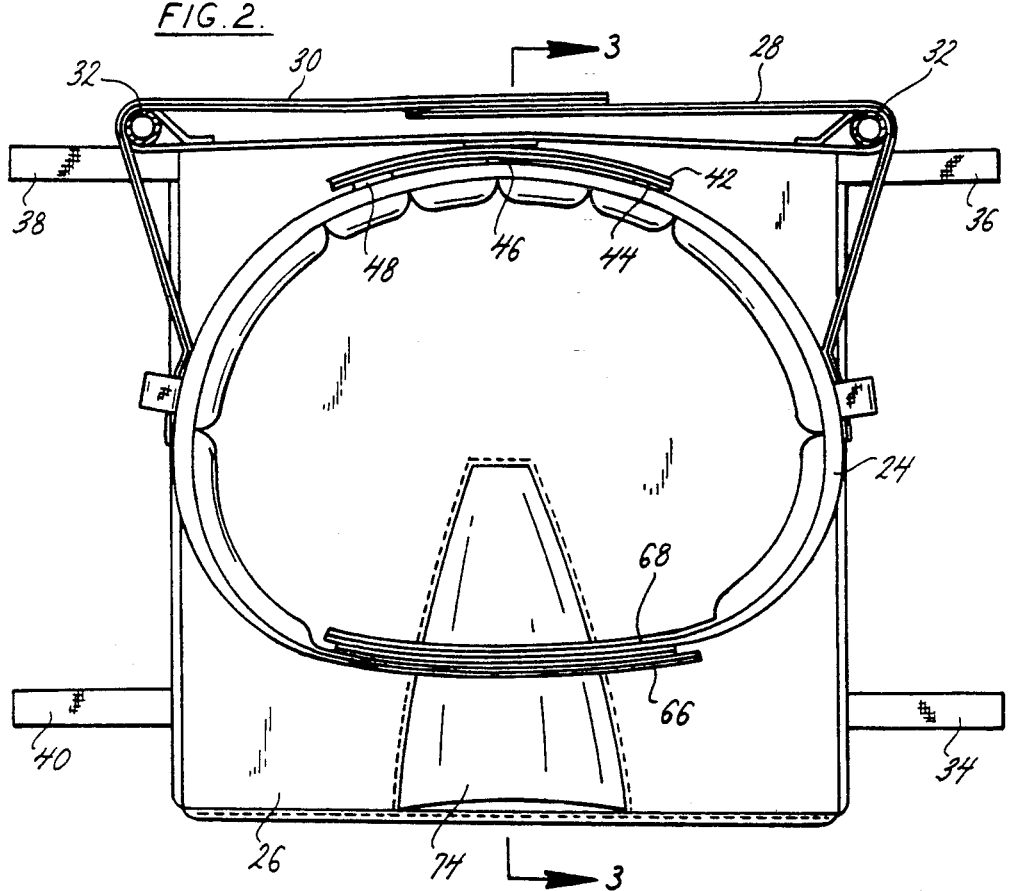
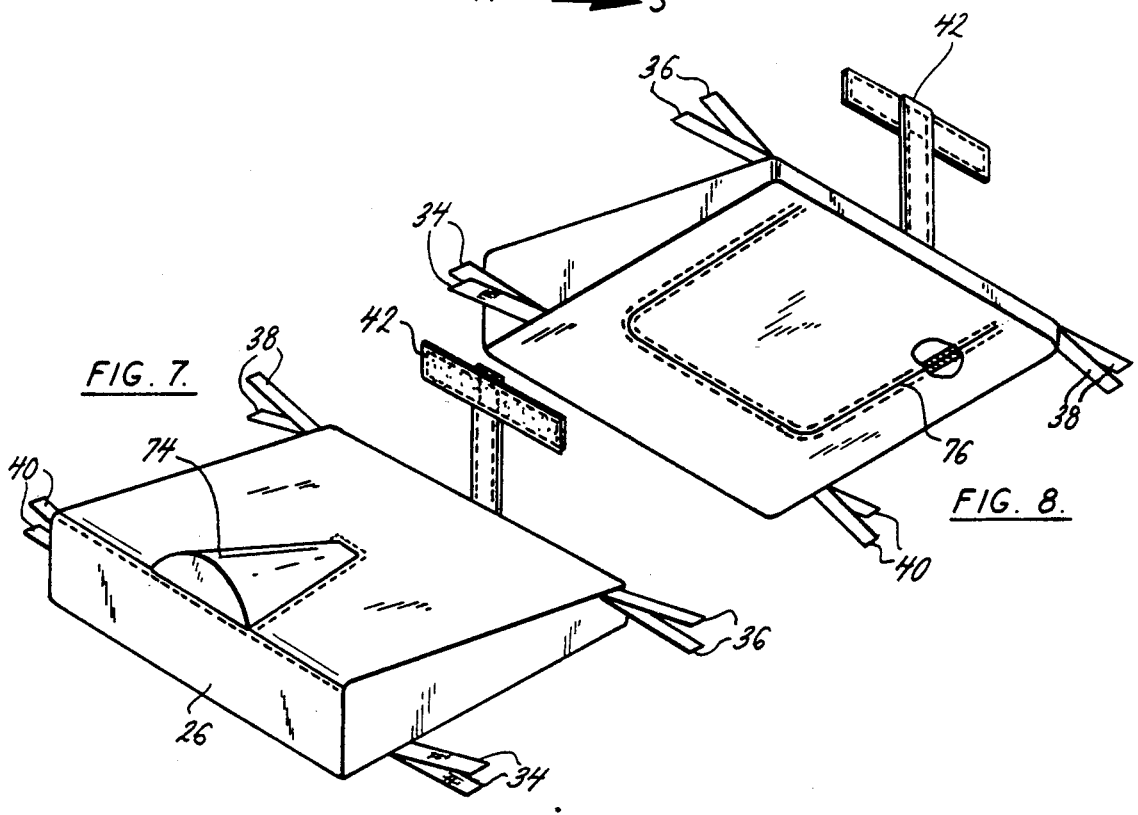

CUSTOM ORTHOTIC BRACING SYSTEM

BACKGROUND AND SUMMARY OF THE INVENTION

There are patients, both those who are infirm and those who are of advanced age, who are chair ridden and unable to adequately support themselves in an upright sitting position. These patients are ambulatory if they may be properly supported in a chair. This includes not only comfortably supporting the patient, but also securely supporting him in such a manner that he will remain upright and not slumped or slouched down into the chair. This is important not only from the standpoint of the patient's comfort, and to prevent any injury to the patient, but also to prevent any further deterioration in the patient's spinal alignment.

In the prior art, there are several devices which are readily available and which attempt to meet this need. Unfortunately, they generally consist of not much more than cushioned straps which hold the patient's torso against the back of the chair and, in some instances, a seat cushion. Of course, these prior art devices do restrain a patient, but do not provide a comfortable and adequate means for supporting the patient as he sits in the chair. First of all, there is a significant range of torsos, and these restraints are typically only adjustable in the length of the strap which surrounds the patient's torso. Nor is there any structure to provide lateral support by these prior art devices as they, for the most part, rely on the chair frame. Furthermore, the straps fit only haphazardly about the patient and, in some instances, can unduly restrict the patient or be uncomfortable because of the size of the particular patient. For example, an obese patient would experience some degree of unpleasantness by being strapped about his lower torso. Similarly, a large woman with large breasts would experience unpleasantness with a strap wrapped around her breast area.

In order to satisfy the deficiencies of the prior art, and as a dramatic improvement thereon, the inventors herein have succeeded in designing and developing a chair restraint which for the first time provides orthotic support independently of the chair frame which may be custom fit to the individual torso of the particular patient. Furthermore, this orthotic support provides lateral support as it includes wing panels which extend around the sides of the patient's torso to more effectively contain the patient within the support without relying on excessively tightened straps. Therefore, the patient is not only more comfortable, but is more effectively supported laterally within the restraint. Straps wrapped around the patient's upper torso prevent the patient from falling directly forward out of the restraint. However, it is believed that the back and lateral restraints significantly decrease the required strap tightness to adequately secure the patient within the restraint and prevent his slouching or slumping in the chair.

In addition to an upper torso restraint member, a seat cushion member aids in effectively cradling the patient within the restraint and in place within the chair. The seat cushion is inclined rearwardly towards the back of the chair and has a center divider piece extending generally down the middle of the seat cushion to thereby form two areas for receiving the patient's legs. The patient's legs are thus cradled between the center piece and each side of the chair. The seat cushion and upper torso members are strapped together, and to the chair frame, to thereby reliably and securely restrain the patient therewithin.

The orthotic support is provided by a readily deformable plastic spine or back member which is readily removable from within the upper torso restraint member through Velcro TM closures or the like. This orthotic panel member is readily deformable with a heat gun or the like such that a technician or nurse may custom fit the panel to the particular patient with which the restraint is intended for use. After being custom fit, the panel may then be readily re-inserted into the upper torso restraint member such that the back and two sides of the patient are "caged" within the upper restraint member. In this manner, a patient may be comfortably and securely restrained in a chair.

While the principal advantages and features of the present invention have been described above, a more complete and thorough understanding of the invention may be attained by referring to the drawings and description of the preferred embodiment which follow.

BRIEF DESCRIPTION OF THE DRAWINGS

FIG. 1 is a perspective view of the chair restraint of the present invention as mounted in a chair;

FIG. 2 is a top view of the chair restraint;

FIG. 4 is a perspective view of the upper torso restraint member only;

FIG. 5 is a partial back view of the restraint detailing the means for securing the seat cushion to the upper restraint member;

FIG. 6 is a partial cross-sectional view taken along the plane of line 6—6 in FIG. 5 and detailing the mounting of the upper torso member to the seat cushion;

FIG. 7 is a perspective view of the seat cushion member only;

FIG. 8 is a bottom view of the seat cushion member only; and

DETAILED DESCRIPTION OF THE PREFERRED EMBODIMENT

Figure 9:
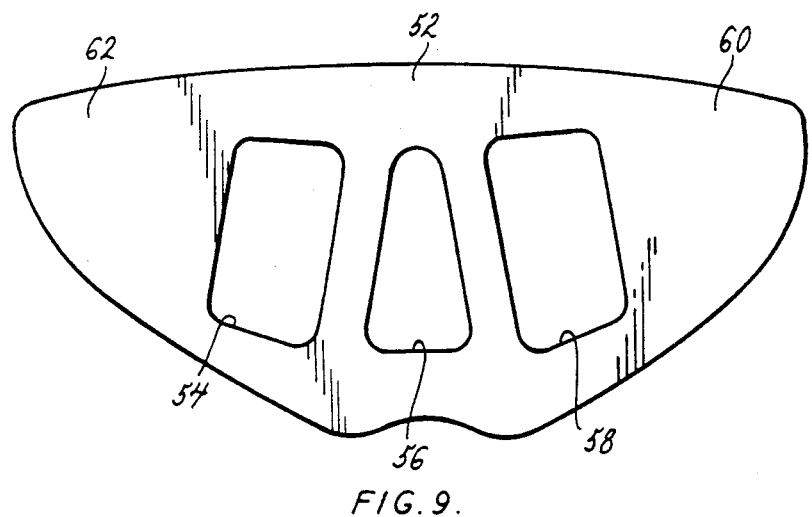
FIG. 9 is a front view of the orthotic support panel separated from the chair restraint.
Figure 3:
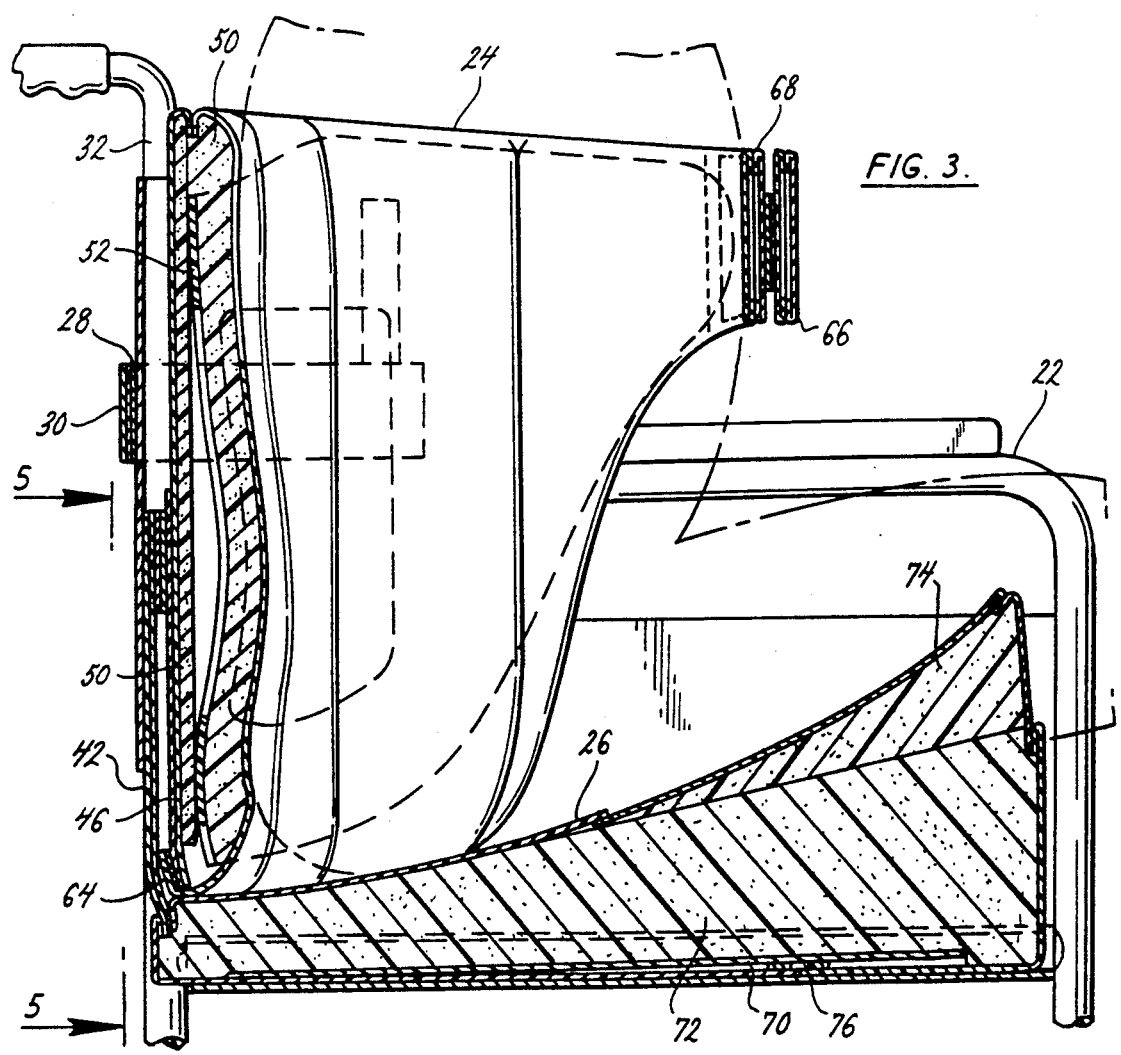
FIG. 3 is a partial cross-sectional view taken along the plane of line 3—3 in FIG. 2 and detailing the application of the chair restraint to a patient.

As shown in FIG. 1, the chair restraint 20 of the present invention is designed to be conveniently strapped into a standardized chair 22 and includes an upper torso restraint member 24 and a seat cushion member 26. As shown in FIG. 2, the upper torso restraint member 24 includes a pair of straps 28, 30 which secure it to the back frame members 32 of chair 22. Similarly, at its four corners, seat cushion 26 includes four pairs of straps 34, 36, 38, 40 for securing the seat cushion member 26 to side frame members (not detailed) of chair 22. Thus, each of upper torso restraint member 24 and seat cushion member 26 are individually secured to the frame of chair 22. Additionally, as is best shown in FIGS. 5, 7 and 8, seat cushion member 26 has a T-strap 42 extending generally upwardly from the back thereof and the upper torso restraint member 24 has three stripes 44, 46, 48 of matching Velcro TM material which is conveniently used for securing seat cushion member 26 to upper torso restraint member 24. Thus, the chair restraint 20 is comprised of an upper torso restraint member 24, and a seat cushion member 26, both of which are individually strapped to the chair and to each other to thereby provide a safe and secure basis for restraining a patient.

As shown in FIGS. 1, 2, 3, 4, 6, and 9, the upper torso restraint member 24 is of multi-layer construction including several inner layers of cushioning material 50 into which is inserted an orthotic support panel 52 (as shown in FIG. 9). As shown more specifically in FIG. 9, the orthotic support panel 52 has three openings 54, 56, 58 therein which give it added flexibility. Additionally, wing members 60, 62 extend generally laterally from the center area of orthotic support panel 52 and are adapted to extend generally forwardly to thereby surround (at least partially) the sides of the patient and provide lateral support. The orthotic support panel 52 may be made of any readily deformable plastic, such as Kydex TM, to facilitate its being custom fit to a patient's torso to thereby maximize its support capabilities for each individual patient. In operation, the orthotic support panel 52 is removed from the upper torso restraint member 24 through an opening along its lower edge secured by Velcro TM flap members 64, as best shown in FIG. 6. After it is separated from the upper torso restraint member 24, the nurse, technician or the like will then custom fit the panel by using a heat gun or the like, as is well known in the art, to fit the panel to the particular patient's torso. Then, the orthotic support panel 52 is reinserted in the upper torso restraint member 24 and the Velcro TM flaps 64 are closed to secure it therewithin. After the patient is placed in the chair, Velcro TM straps 66, 68 are secured about the patient's torso and thereby restrain him within the chair.

The seat cushion member 26 is best shown in FIGS. 2, 3, 7, and 8, and has an inner stiffening panel 70 which is generally flat to provide a base for support of the patient, and a generally inclined seat cushion 72 which inclines rearwardly towards the back of the chair and the patient's torso. A center, upwardly protruding, cushion member 74 separates the two sides of the seat cushion 26 and provides areas for receiving the patient's legs to help retain them in place and prevent them from inadvertently crossing. The seat cushion 72 and stiffener panel 70 are accessible through the bottom of seat cushion member 26 through a zippered opening 76.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A restraint for the torso of a patient to support said patient in the sitting position in a chair, said restraint including a cage-like stiffening panel of sufficient width for surrounding a substantial portion of the back and sides of said torso, cushioning means surrounding said restraint, and means for securing said restraint to a chair for stabilizing said restraint, said restraint thereby providing lateral restraint.

2. The restraint of claim 1 wherein said stiffening panel is deformable to thereby permit its being fitted to an individual patient.

3. The restraint of claim 2 wherein said stiffening panel is made from a heat deformable plastic.

4. The restraint of claim 1 wherein said stiffening panel includes a back portion, and a wing portion extending generally laterally from each side of said back portion.

5. The restraint of claim 4 further comprising a seat cushion, said seat cushion having an upper surface formed at an incline sloping downwardly towards the back portion of said stiffening panel and an elevated medial divider member extending from the front of the seat cushion and rearwardly to thereby provide two defined areas for receiving the patient's legs.

6. The restraint of claim 5 further comprising means for adjustably securing the seat cushion thereto and to a chair seat or the like.

7. The restraint of claim 6 wherein said securing means and said adjustable securing means comprise straps.

8. The restraint of claim 7 wherein said chair is a wheelchair.

9. The restraint of claim 1 wherein said stiffening panel is integrally formed and includes a plurality of openings therein.

10. A restraint for supporting a patient in a sitting position, said restraint having a removable panel member, said panel member being readily deformable to permit said panel member to be custom fit to any individual patient, said panel member being of sufficient width to fit snugly about the patient's torso, and means for securing said restraint to a chair or the like to thereby secure said patient into an upright sitting position.

11. The restraint of claim 10 further comprising a seat cushion member, means for securing said panel member to said seat cushion member, and said seat cushion member having a center divider member to thereby form two areas of said seat cushion for receiving the patient's two legs.

12. The restraint of claim 11 wherein said seat cushion leg areas are inclined towards the patient's torso to thereby help cradle the patient within the restraint.

13. The restraint of claim 12 further comprising a cushioning enclosure, said panel member being retained in said cushioning enclosure and readily removable therefrom.

14. The restraint of claim 13 further comprising straps for surrounding said patient to thereby secure said restraint to said patient.

15. The restraint of claim 10 wherein said removable panel member includes a back portion, and a wing portion extending generally laterally from each side of said back portion.

16. The restraint of claim 15 wherein said removable panel member is integrally formed and includes a plurality of openings in its back portion.

17. The restraint of claim 16 wherein said stiffener is made of heat deformable plastic to thereby facilitate its custom fit to any individual patient.

18. The restraint of claim 17 wherein said chair is a wheelchair.

19. A restraint for the torso of a patient to support said patient in the sitting position, said restraint including a stiffener for substantially surrounding the back and sides of a patient's torso, said stiffener including a back portion, and a wing portion extending generally laterally from each side of said back portion, said stiffener being integrally formed and including a plurality of openings in its back portion, a belt means extending from one side of said restraint to the other thereof for securing said restraint around the patient's torso, and means for securing said restraint to a seat back or the like to thereby stabilize said restraint.

20. The restraint of claim 19 wherein said stiffener is made of heat deformable plastic, and further comprising means for removing said stiffener from said restraint and replacing said stiffener into said restraint.

21. The restraint of claim 20 wherein said back portion is substantially taller than said wing portions to thereby extend from a point proximate the bottom of a patient's back as he sits to a point proximate a patient's underarms, said wings extending generally forwardly at the top of each side to a point proximate the chest and from the bottom sloping upwardly to the patient's chest, each wing thereby tapering forwardly and upwardly.

22. The restraint of claim 21 wherein said chair is a wheelchair.

* * * * *